(12) United States Patent
Anantharaman

(10) Patent No.: US 7,959,353 B2
(45) Date of Patent: Jun. 14, 2011

(54) INFRA-RED THERMAL IMAGING OF LASER WELDED BATTERY MODULE ENCLOSURE COMPONENTS

(75) Inventor: Satish Anantharaman, Rochester, MI (US)

(73) Assignee: Cobasys, LLC, Orion, MI (US)

( * ) Notice: Subject to any disclaimer, the term of this patent is extended or adjusted under 35 U.S.C. 154(b) by 225 days.

(21) Appl. No.: 12/330,787

(22) Filed: Dec. 9, 2008

(65) Prior Publication Data
US 2009/0087083 A1  Apr. 2, 2009

Related U.S. Application Data

(62) Division of application No. 11/211,021, filed on Aug. 24, 2005.

(51) Int. Cl.
*G01K 9/00* (2006.01)
(52) U.S. Cl. .............................. 374/4; 374/120; 374/141
(58) Field of Classification Search .............. 374/4, 120, 374/141
See application file for complete search history.

(56) References Cited

U.S. PATENT DOCUMENTS

| | | | | |
|---|---|---|---|---|
| 4,168,430 A | * | 9/1979 | Denis et al. | 250/338.1 |
| 4,214,164 A | * | 7/1980 | Traub et al. | 250/338.1 |
| 4,663,513 A | * | 5/1987 | Webber | 219/121.6 |
| 4,847,462 A | | 7/1989 | Soodak et al. | |
| 4,854,724 A | * | 8/1989 | Adams et al. | 374/5 |
| 5,250,809 A | * | 10/1993 | Nakata et al. | 250/330 |
| 5,279,693 A | | 1/1994 | Robinson et al. | |
| 5,382,770 A | | 1/1995 | Black et al. | |
| 5,478,426 A | | 12/1995 | Wiler et al. | |
| 5,893,959 A | | 4/1999 | Muellich | |
| 6,262,387 B1 | | 7/2001 | Chang | |
| 6,828,054 B2 | | 12/2004 | Appleby et al. | |
| 6,866,962 B2 | | 3/2005 | Bechtold et al. | |
| 2002/0008086 A1 | * | 1/2002 | Fujii et al. | 219/110 |
| 2002/0134817 A1 | * | 9/2002 | Shepard | 228/105 |
| 2004/0114662 A1 | * | 6/2004 | Messler | 374/130 |
| 2004/0134983 A1 | | 7/2004 | Oyama et al. | |
| 2005/0169346 A1 | | 8/2005 | Murray, Jr. et al. | |
| 2007/0167782 A1 | * | 7/2007 | Callahan et al. | 600/443 |

FOREIGN PATENT DOCUMENTS

| | | |
|---|---|---|
| DE | 4311320 A1 | 10/1994 |
| DE | 19650883 A1 | 6/1998 |
| DE | 19920219 A1 | 11/2000 |
| EP | 1371443 A1 | 12/2003 |
| JP | 2005223151 | 8/2005 |

OTHER PUBLICATIONS

Database WPI Week 200560; Derwent Publications Ltd., London G; AN 2005-586149 XP002417431 & JP2005223151 A (Taiyo Denki KK) Aug. 18, 2005; 1 page.

* cited by examiner

*Primary Examiner* — Lisa M Caputo
*Assistant Examiner* — Mirellys Jagan

(57) ABSTRACT

A thermal imaging system for a battery module enclosure that includes first and second battery module enclosure components between which a weld is formed includes a thermal imaging camera that focuses on the first and second battery module enclosure components within a predetermined amount of time after the weld is formed and that acquires a thermal signature. A control module includes an image processing module that receives the thermal signature and that locates a predetermined reference point in the thermal signature. An image comparison module receives the thermal signature and uses the predetermined reference point to compare the thermal signature to a template signature in order to verify structural integrity of the weld. The image comparison module computes a relative measure of deviation of the thermal signature from the template signature and identifies the weld as defective when the relative measure of deviation is greater than a predetermined value.

8 Claims, 5 Drawing Sheets

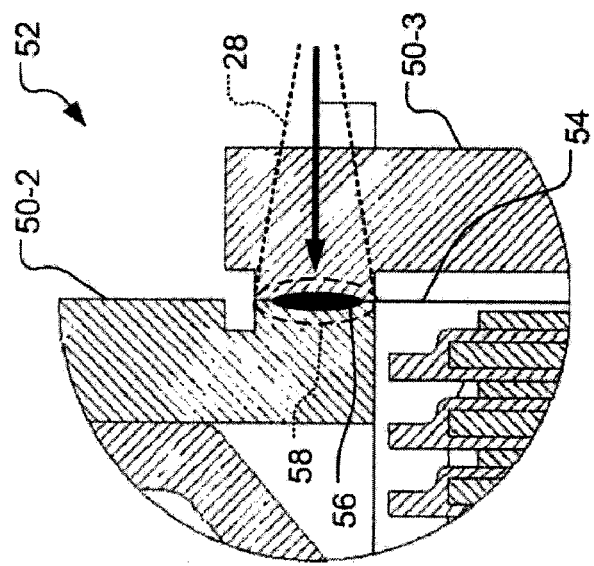
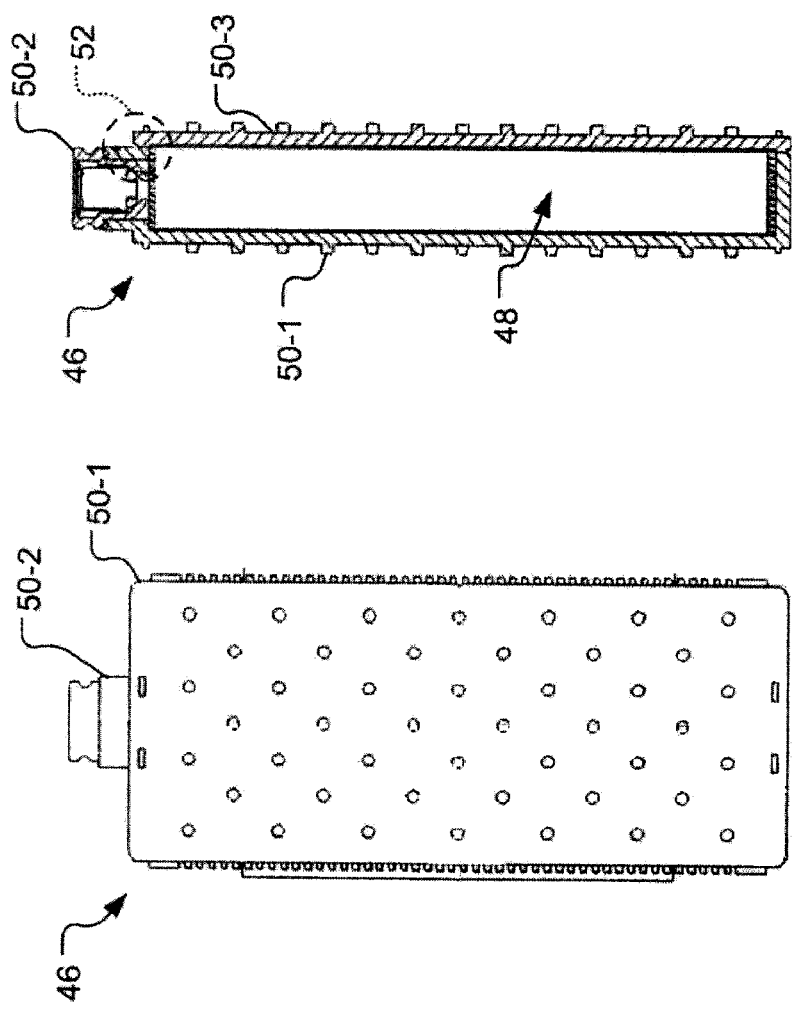
*FIG. 2A*
*FIG. 2B*
*FIG. 2C*

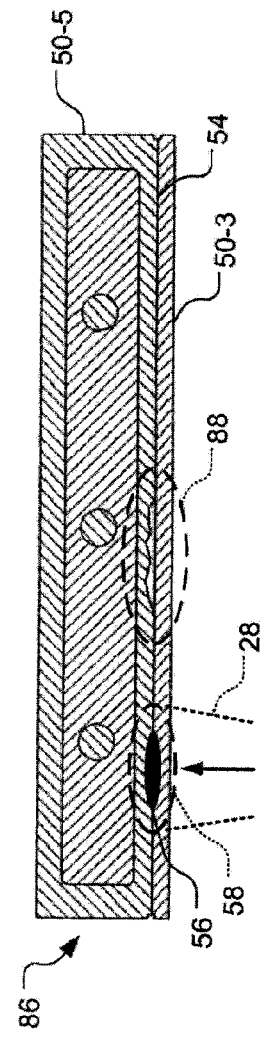
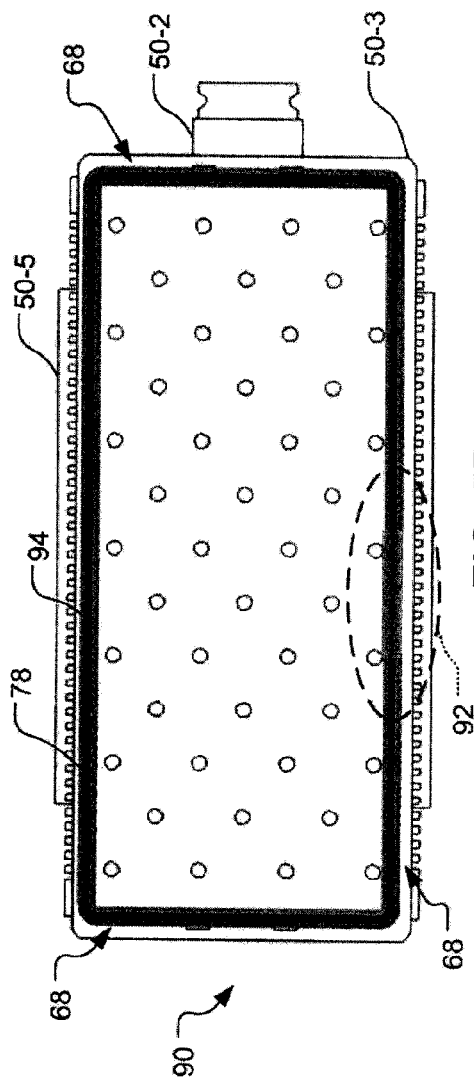
FIG. 4
FIG. 5A
FIG. 5B

INFRA-RED THERMAL IMAGING OF LASER WELDED BATTERY MODULE ENCLOSURE COMPONENTS

CROSS-REFERENCE TO RELATED APPLICATIONS

This application is a Divisional Application of U.S. patent application Ser. No. 11/211,021, filed Aug. 24, 2005. The entire disclosure of the above application is incorporated herein by reference.

FIELD OF THE INVENTION

The present invention relates to thermal imaging of plastic welds, and more particularly to infra-red thermal imaging of thermoplastic components used in battery module enclosures.

BACKGROUND OF THE INVENTION

Battery module enclosures house one or more battery cells that are utilized to provide electrical power. For example, a battery module enclosure may include multiple battery cells connected in series to provide a desired voltage. In some cases, the battery cells comprise liquid materials such as potassium hydroxide and require airtight sealing from an exterior of the battery module as well as between individual cells to prevent a short-circuit condition. Additionally, the battery modules are often utilized in physically unstable environments such as vehicles for hybrid electric applications. Therefore, battery module enclosures commonly comprise thermoplastic materials such as polymeric blends. Since the battery module enclosures typically include at least two interfacing components, welding is often required to create a seal between the multiple components.

Ideally, such welding results in electrically isolated cell pockets. However, variation among plastic components used to make the battery module enclosures creates the possibility of weak or even non-existent welds at defective regions. For example, variations may occur during a molding process or during shipping or handling of plastic components. In one approach, quality control and inspection techniques are used to detect external leakage and/or identify weak welds. However, external inspection of battery module enclosures cannot identify internal leakage or weak welds that are not visibly apparent. Additionally, it is costly and time consuming to manually inspect every weld of every plastic enclosure component that is manufactured.

SUMMARY OF THE INVENTION

A thermal imaging system for a battery module enclosure that includes first and second battery module enclosure components between which a weld is formed according to the present invention includes a thermal imaging camera that focuses on the first and second battery module enclosure components within a predetermined amount of time after the weld is formed and that acquires a thermal signature. A control module includes an image processing module that receives the thermal signature and that locates a predetermined reference point in the thermal signature. An image comparison module receives the thermal signature and uses the predetermined reference point to compare the thermal signature to a template signature in order to verify structural integrity of the weld.

In other features, the thermal imaging camera is an infra-red thermal imaging camera. The image processing module utilizes an image processing algorithm that locates a structural feature that is common to both of the thermal and template signatures. The first and second battery module enclosure components comprise polymeric thermoplastics. The battery module enclosure houses at least one battery cell for a hybrid electric vehicle. A laser source focuses a laser beam on the first and second module enclosure components in order to form the weld. The first and second module enclosure components are fixed on a turntable that includes a motor. The control module includes a turntable module that adjusts a position of the turntable so that the first and second module enclosure components are located within a path of the laser beam when the laser source forms the weld and so that the first and second module enclosure components are within a field of view of the thermal imaging camera when the thermal imaging camera acquires the thermal signature.

In still other features of the invention, the image comparison module computes a relative measure of deviation of the thermal signature from the template signature and identifies the weld as defective when the relative measure of deviation is greater than a predetermined value. A data module stores the template signature. The image comparison module stores the thermal signature and a weld integrity value that is associated with the thermal signature in the data module after the image comparison module verifies structural integrity of the weld. A data analysis module generates weld integrity statistics based on a plurality of weld integrity values that are stored in the data module.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 2A is a front view of an exemplary single-cell battery module enclosure;

FIG. 2B is a side cross-section of the single-cell battery module enclosure illustrating interfaces between plastic battery module enclosure components;

FIG. 2C is a scaled partial view of FIG. 2B illustrating a weld made between the plastic enclosure components using laser welding;

FIG. 4 illustrates an exemplary thermal signature gradient that identifies visual image fluctuations in thermal signatures due to temperature variations;

FIG. 5A is a second cross-section of the single-cell battery module enclosure illustrating a defect in the plastic enclosure components;

FIG. 5B is a thermal signature of the single-cell battery module enclosure of FIG. 5A from a top view perspective that illustrates a visual inconsistency at the defective region.

DETAILED DESCRIPTION OF THE PREFERRED EMBODIMENTS

Figure 1:
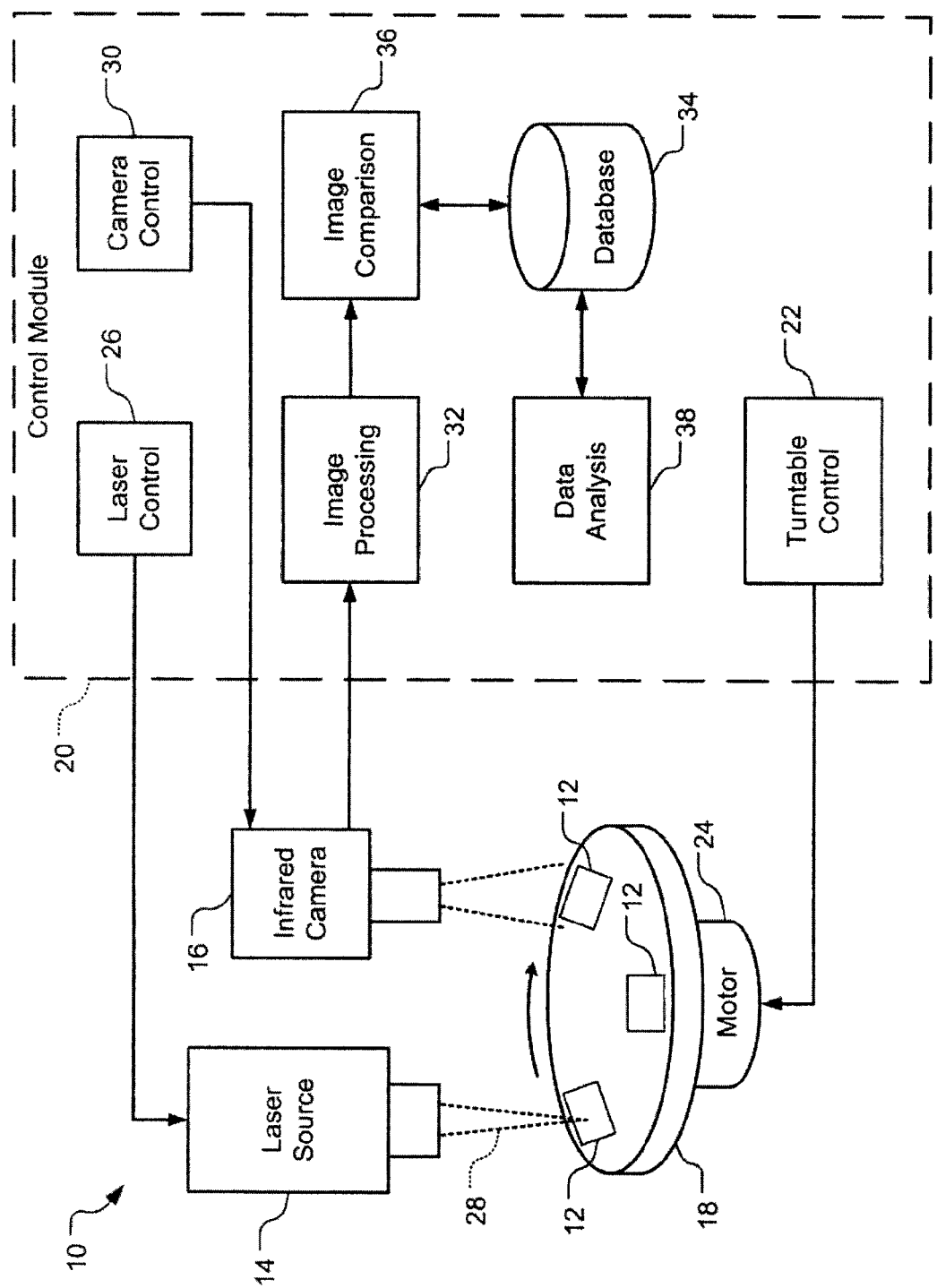
FIG. 1 is a functional block diagram of a thermal imaging system for plastic enclosure components of a battery module according to the present invention.

The following description of the preferred embodiment(s) is merely exemplary in nature and is in no way intended to limit the invention, its application, or uses. For purposes of clarity, the same reference numbers will be used in the drawings to identify similar elements. As used herein, the term module refers to an application specific integrated circuit (ASIC), an electronic circuit, a processor (shared, dedicated, or group) and memory that execute one or more software or firmware programs, a combinational logic circuit, and/or other suitable components that provide the described functionality.

Referring now to FIG. 1, an exemplary thermal imaging system 10 for a battery module enclosure 12 includes a laser source 14, an infra-red thermal imaging camera 16, and a turntable 18. Plastic enclosure components 12 that are desired for welding are fixed to the turntable 18. For example, the turntable 18 may move the plastic enclosure components 12 between three different positions. At a first position, the plastic enclosure components 12 are fixed to the turntable 18. The plastic enclosure components 12 are moved to a second position where the laser source 14 generates welds at junctions between two or more plastic enclosure components 12. Lastly, the plastic enclosure components 12 are moved to a third position where the infra-red thermal imaging camera 16 captures a thermal signature in order to verify the integrity of the welds.

A control module 20 controls operation of the thermal imaging system 10. The control module 20 includes a turntable control module 22 that communicates with a motor 24 of the turntable 18 and adjusts a position of the turntable 18 during welding and thermal imaging of the plastic enclosure components 12. For example, the turntable control module 22 may be programmed to rotate the turntable 18 a predetermined number of degrees between each of the positions. A laser control module 26 controls operation of the laser source 14. For example, the laser control module 26 turns the laser source 14 on and off and may adjust operational parameters of the laser source 14 such as a wavelength of a laser beam 28 that the laser source 14 emits. A camera control module 30 controls operation of the infra-red thermal imaging camera 16. For example, the camera control module 30 turns the infra-red thermal imaging camera 16 on and off and may adjust operational parameters such as resolution and zoom.

In an exemplary embodiment, the plastic enclosure components 12 comprise thermoplastics such as polymeric blends. Since thermoplastics are poor conductors, the weld temperatures of the plastic enclosure components 12 remain consistent for a period of time. Therefore, the infra-red thermal imaging camera 16 preferably acquires thermal signatures of the welded plastic enclosure components 12 within a predetermined amount of time after the welding procedure is completed. For example, the infra-red thermal imaging camera 16 may be set to acquire the thermal signatures within five seconds after a welding procedure is performed.

An image processing module 32 receives thermal signatures corresponding to the plastic enclosure components 12 from the infra-red thermal imaging camera 16. A database 34 includes a template signature corresponding with plastic enclosure components 12 that have predetermined satisfactory welds. For example, a template signature may correspond with plastic enclosure components 12 that are rigorously inspected using microscopic technology to ensure satisfactory welds. The template signature includes one or more reference points that correspond with structure that is common to both the template signature and other potential thermal signatures. Therefore, the image processing module 32 utilizes an image processing algorithm to locate a reference point on a thermal signature that corresponds with a reference point on the template signature. For example, the reference point may be a visible surface or edge of the plastic enclosure components 12.

An image comparison module 36 receives the thermal signature from the image processing module 32 and the template signature from the database 34. The image comparison module 36 compares the thermal and template signatures to detect defective plastic enclosure components 12 or weak or nonexistent welds. For example, the image comparison module 36 may detect visual inconsistencies in the thermal signature along junctions where the plastic enclosure components 12 are welded. Based on the comparison, the image comparison module 36 determines whether the plastic enclosure components 12 are satisfactory or unsatisfactory. For example, the image comparison module 36 may compute a relative measure of deviation of the thermal signature from the template signature. A satisfactory thermal signature may correspond with a relative measure of deviation that is less than or equal to a predetermined value. For example, the predetermined value may be adjusted depending on a desired tolerance with which to inspect the plastic enclosure components 12.

Additionally, following the signature comparison the image comparison module 36 stores the thermal signature in the database 34 with the associated satisfactory or unsatisfactory identifier. The control module 20 includes a data analysis module 38 that reads stored thermal signature test results in the database 34 and generates weld integrity statistics. For example, the data analysis module 38 may track the relative rate of occurrence of defective welds for quality control purposes.

Referring now to FIGS. 2A-2C, an exemplary battery module 46 includes an inner cavity 48 that houses a battery cell. The inner cavity 48 is defined by multiple plastic enclosure components 50 that interface and are welded together along junctions between the plastic enclosure components 50. For example, FIG. 2C illustrates an enlarged view 52 of a junction 54 between side and top plastic enclosure components 50-3 and 50-2, respectively, of the battery module 46. A through transmission laser welding (TTLW) process is used to focus the laser beam 28 at the junction 54. For example, the laser source 14 may include a plurality of laser beams 28 that are utilized to continuously illuminate a desired area, although other laser source configurations are possible. A melt pool 56 forms within a heat zone 58, which leaves a structural bond between the plastic enclosure components 50-2 and 50-3 when the laser source 14 is turned off and the melt pool 56 cools.

Since thermoplastics typically have a low conductivity and the laser source 14 has high focusing capabilities, the heat zone 58 is relatively small and presents little risk to components housed in the inner cavity 48. While the battery module 46 illustrated in FIGS. 2A-2C is a single-cell battery module 46, those skilled in the art can appreciate that battery modules 46 may include multiple battery cells that are individually isolated and connected in series.

Figure 3A:
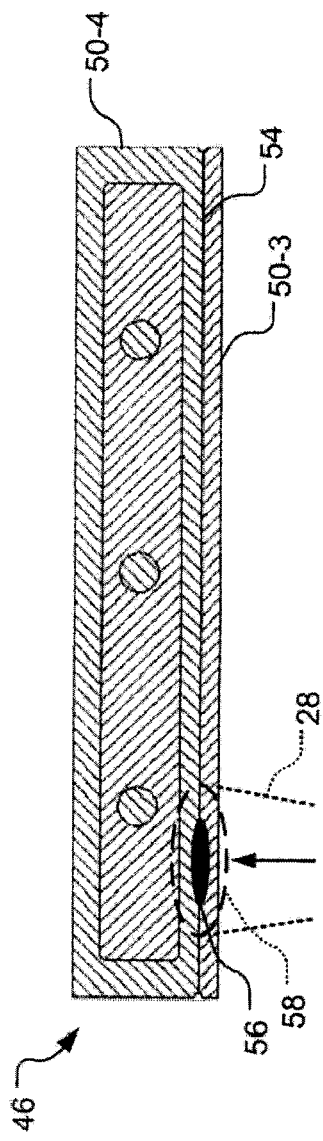
FIG. 3A is a first cross-section of the single-cell battery module enclosure illustrating welding along an interface between two plastic enclosure components.
Figure 3B:
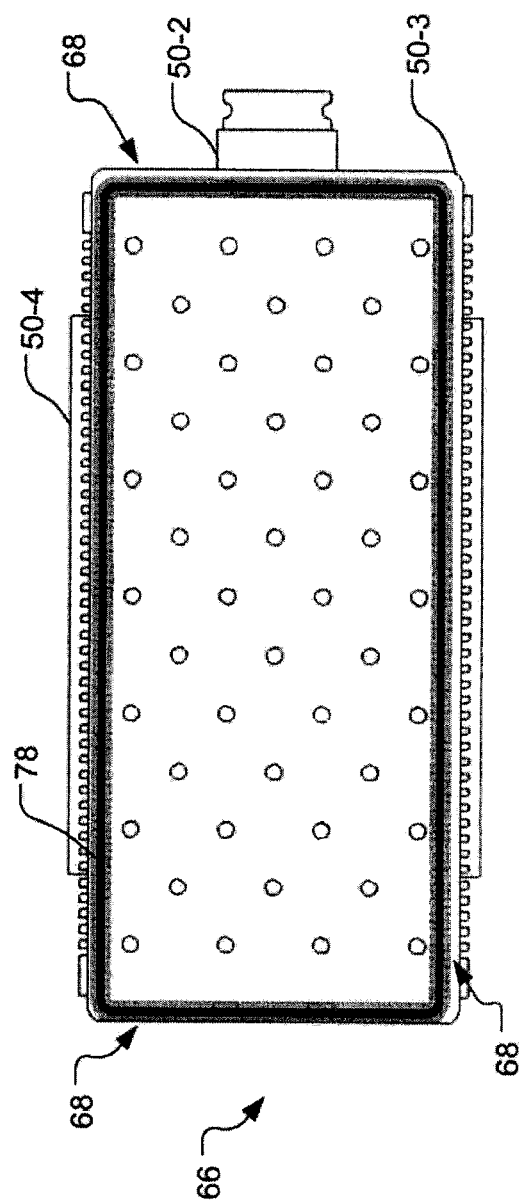
FIG. 3B is a thermal signature of the single-cell battery module enclosure of FIG. 3A from a top view perspective following a welding procedure.

Referring now to FIGS. 3A and 3B, in order for a laser beam 28 to reach the junction 54 between plastic enclosure components 50, at least one of the plastic enclosure components 50-4 and/or 50-3 is transmissive to a wavelength of the laser beam 28. In an exemplary embodiment, the wavelength of the laser beam 28 is between 800 nm and 1100 nm, although other wavelengths are possible. The laser beam 28 penetrates plastic enclosure component 50-3 to create the heat zone 58 at the junction 54 between the plastic enclosure components 50. FIG. 3A illustrates plastic enclosure components 50 that are free of defects prior to welding, and welds are made along a perimeter of the plastic enclosure components 50 to seal the battery module 46 during the welding process. FIG. 3B shows a top view of the thermal signature 66 for the plastic enclosure components 50. Temperature differences at weld points 68 along the perimeter of the battery module 46 are indicated by fluctuating colors on the thermal signature 66.

Referring now to FIG. 4, an exemplary thermal signature gradient 76 illustrates the appearance of varying temperatures on thermal signatures 66. For example, according to the thermal signature gradient 76, temperatures below room temperature do not stand out in the thermal signature 66 and temperatures required for thermoplastic welding appear very dark or opaque. Therefore, colors remain consistent with expected temperatures along weld points 68 as illustrated in FIG. 3B. Interior portions 78 (as shown in FIG. 3B) of the weld points 68 appear very dark along the perimeter of the plastic enclosure components 50, and the colors lighten when moving away from the interior portions 78.

Referring now to FIGS. 5A and 5B, a plastic enclosure component 50-5 of a battery module 86 is defective. For example, a chip 88 in the plastic enclosure component 50-5 may prevent a structurally sound weld from being generated at the junction 54 between two plastic enclosure components 50-3 and 50-5. FIG. 5B shows a top view of a thermal signature 90 for the battery module 86 of FIG. 5A. The consistency in color of the thermal signature 90 along the weld points 68 is broken at an area 92 where the chip 88 is located. The typically dark color of the interior portion 78 of the weld points 68 is missing and is replaced with a lighter color consistent with outer portions 94 of weld points 68. The image processing algorithm executed by the image processing module 32 detects the inconsistency in the thermal signature 90 and identifies the battery module 86 as defective before storing the thermal signature 90 in the database 34.

Figure 6:
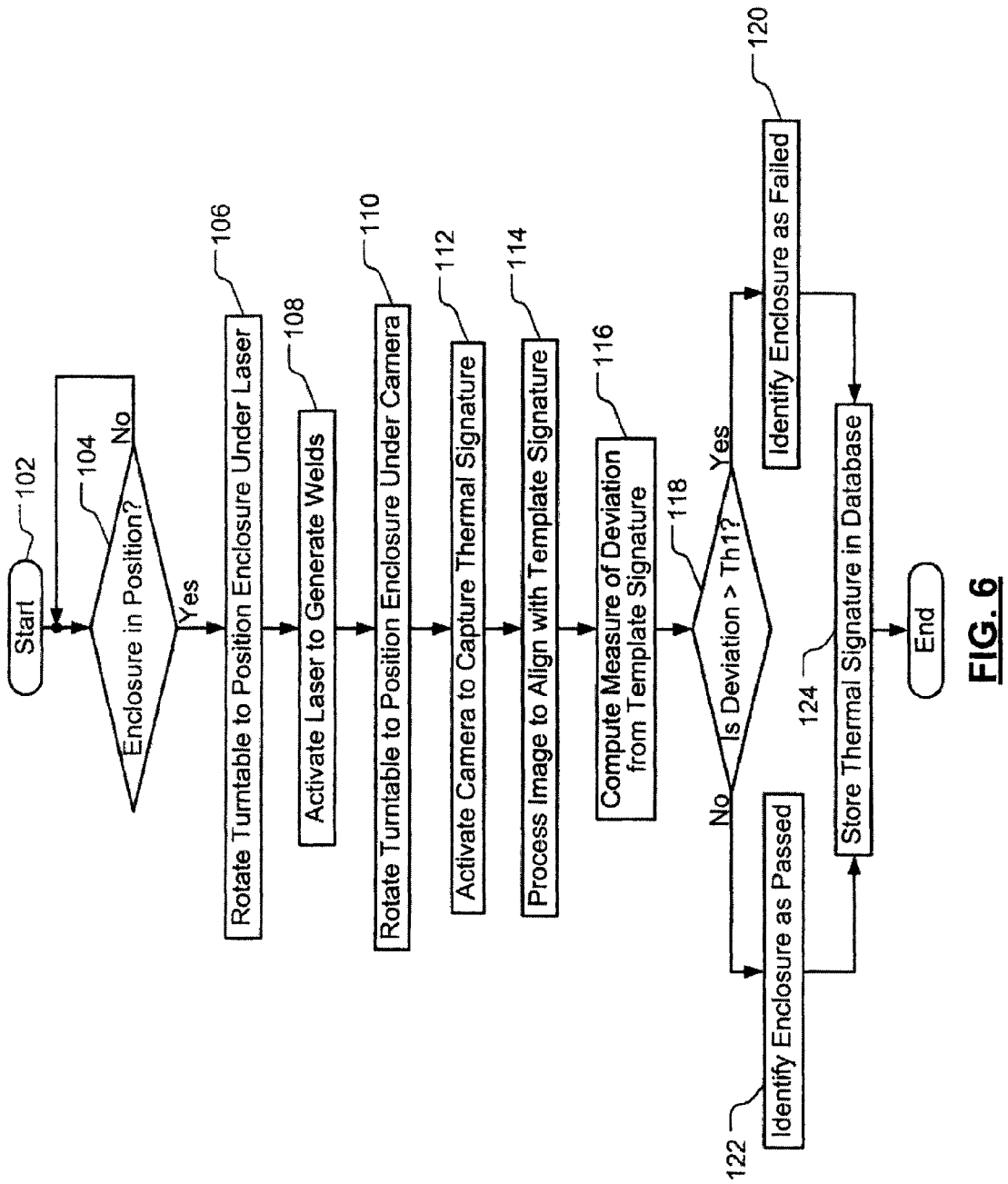
FIG. 6 is a flowchart illustrating steps performed by the thermal imaging system to detect defective welds.

Referring now to FIG. 6, a thermal imaging algorithm begins in step 102. In step 104, control determines whether the next plastic enclosure components 50 desired for welding are in position. If false, control loops to step 104. If true, the turntable control module 22 adjusts a position of the turntable 18 so that the plastic enclosure components 50 are situated under the laser source 14 for welding in step 106. In step 108, the laser control module 26 activates the laser source 14 to generate the welds. In step 110, the turntable control module 22 adjusts a position of the turntable 18 so that the plastic enclosure components 50 are situated within a field of view of the infra-red thermal imaging camera 16. In step 112, the camera control module 30 activates the infra-red thermal imaging camera 16 in order to acquire a thermal signature 90 of the plastic enclosure components 50.

In step 114, the image processing module 32 receives the thermal signature 90 and locates a reference point that is consistent with the template signature 66. In step 116, the image comparison module 36 compares the thermal and template signatures 90 and 66, respectively, and computes a relative measure of deviation of the thermal signature 90 from the template signature 66. In step 118, control determines whether the relative deviation is greater than a predetermined value. If true, control proceeds to step 120. If false, the image comparison module 36 identifies the battery module 86 as satisfactory in step 122 and control proceeds to step 124. In step 120, the image comparison module 36 identifies the battery module 86 as defective and control proceeds to step 124. In step 124, the image comparison module 36 stores the thermal signature 90 in the database 34 and control ends.

The thermal imaging system 10 of the present invention is utilized to verify proper welding of plastic enclosure components 50 of battery modules 86 such as battery cells for hybrid electric vehicles. The thermal imaging system 10 is non-destructive and may be completely integrated with the laser welding process in order to identify defective welds immediately, which lowers costs and reduces manufacturing times.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification, and the following claims.

What is claimed is:

1. A method for operating a thermal imaging system for a battery module enclosure that includes first and second battery module enclosure components between which a weld is formed, comprising:
   fixing the first and second module enclosure components on a turntable;
   adjusting a position of said turntable a first time so that the first and second module enclosure components are located within a path of a laser beam when the weld is formed;
   focusing said laser beam on the first and second module enclosure components in order to form the weld;
   after forming the weld, adjusting said position of said turntable a second time so that the first and second module enclosure components are within a field of view sufficient to obtain a thermal signature of the weld;
   after adjusting said position of said turntable said second time, acquiring a said thermal signature of the weld within a predetermined amount of time after the weld is formed;
   utilizing an image processing algorithm to locate a predetermined reference point in said thermal signature; and
   comparing said thermal signature to a template signature in order to verify structural integrity of the weld.

2. The method of claim 1 further comprising using an infra-red thermal imaging camera to acquire said thermal signature.

3. The method of claim 1 further comprising utilizing an image processing algorithm that locates a structural feature that is common to both of said thermal and template signatures.

4. The method of claim 1 wherein the first and second battery module enclosure components comprise polymeric thermoplastics.

5. The method of claim 1 further comprising housing at least one battery cell for a hybrid electric vehicle in the battery module enclosure.

6. The method of claim 1 further comprising:
   computing a relative measure of deviation of said thermal signature from said template signature; and
   identifying the weld as defective when said relative measure of deviation is greater than a predetermined value.

7. The method of claim 1 further comprising:
storing said template signature in a database;
verifying structural integrity of the weld; and
storing said thermal signature and a weld integrity value that is associated with said thermal signature in said database.

8. The method of claim 7 further comprising generating weld integrity statistics based on a plurality of weld integrity values that are stored in said database.

* * * * *

UNITED STATES PATENT AND TRADEMARK OFFICE
CERTIFICATE OF CORRECTION

| | | |
|---|---|---|
| PATENT NO. | : 7,959,353 B2 | |
| APPLICATION NO. | : 12/330787 | |
| DATED | : June 14, 2011 | |
| INVENTOR(S) | : Satish Anantharaman | |

It is certified that error appears in the above-identified patent and that said Letters Patent is hereby corrected as shown below:

Column 6, Line 43    Delete "a" after "acquiring"

Signed and Sealed this
Eighteenth Day of October, 2011

David J. Kappos
*Director of the United States Patent and Trademark Office*